United States Patent
Stenzel et al.

(10) Patent No.: US 9,138,561 B2
(45) Date of Patent: Sep. 22, 2015

(54) MRI COMPATIBLE HANDLE AND STEERABLE SHEATH

(71) Applicant: IMRICOR MEDICAL SYSTEMS, INC., Burnsville, MN (US)

(72) Inventors: Gregg S. Stenzel, Victoria, MN (US); Bryan A. Brutlag, Minneapolis, MN (US); Steven R. Wedan, Savage, MN (US); Douglas A. Page, Apple Valley, MN (US); Thomas W. Lloyd, Eagan, MN (US); James Alan Kalthoff, Waconia, MN (US)

(73) Assignee: IMRICOR MEDICAL SYSTEMS, INC., Burnsville, MN (US)

( * ) Notice: Subject to any disclaimer, the term of this patent is extended or adjusted under 35 U.S.C. 154(b) by 0 days.

(21) Appl. No.: 14/106,177

(22) Filed: Dec. 13, 2013

(65) Prior Publication Data
US 2014/0100445 A1    Apr. 10, 2014

Related U.S. Application Data (63) Continuation-in-part of application No. 13/819,981, filed as application No. PCT/US2012/069487 on Dec. 13, 2012, now abandoned, application No. 14/106,177, which is a continuation of application No. PCT/US2013/074331, filed on Dec. 11, 2013.

(60) Provisional application No. 61/576,161, filed on Dec. 15, 2011.

(51) Int. Cl.
*A61M 25/01*    (2006.01)
*A61B 5/055*    (2006.01)
(Continued)

(52) U.S. Cl.
CPC .......... *A61M 25/0136* (2013.01); *A61B 5/055* (2013.01); *G01R 33/287* (2013.01);
(Continued)

(58) Field of Classification Search
CPC .......... A61B 5/05; A61M 5/00; A61M 5/32; A61M 31/00; A61M 29/00
USPC ........ 600/410, 411, 463; 604/8, 103.7, 95.04, 604/523, 528; 606/194; 607/122
See application file for complete search history.

(56) References Cited

U.S. PATENT DOCUMENTS 5,507,725 A    4/1996 Savage et al.
5,531,664 A    7/1996 Adachi et al.
(Continued)

FOREIGN PATENT DOCUMENTS

DE    69333140 T2    6/2004
DE    102011121964 A1    6/2013
(Continued)

OTHER PUBLICATIONS

International Search Report and Written Opinion issued by the International Search Authority, U.S. Receiving Office, regarding corresponding patent application Serial No. PCT/US2013/074331, dated Feb. 20, 2014, 15 pages.
(Continued)

*Primary Examiner* — William Thomson
*Assistant Examiner* — Victor Shapiro
(74) *Attorney, Agent, or Firm* — Barbara A. Wrigley; Oppenheimer Wolff & Donnelly LLP (57) ABSTRACT

An MR compatible deflectable catheter and method of using the same is provided. The MR compatible deflectable catheter includes a steerable sheath having a tubular shaft. The tubular shaft receives first and second longitudinal movement wires at a distal end thereof. A control handle is coupled to a proximal end of the first and second longitudinal movement wires and causes longitudinal movement of the wires.

19 Claims, 7 Drawing Sheets

(51) Int. Cl.
*G01R 33/28* (2006.01)
*A61M 25/00* (2006.01)

(52) U.S. Cl.
CPC ........ *A61M25/0052* (2013.01); *A61M 25/0054* (2013.01); *A61M 25/0108* (2013.01); *A61M 25/0127* (2013.01); *A61M 25/0147* (2013.01); *G01R 33/286* (2013.01)

(56) References Cited

U.S. PATENT DOCUMENTS

| | | | |
|---|---|---|---|
| 5,545,200 A * | 8/1996 | West et al. | 607/122 |
| 5,603,697 A | 2/1997 | Grundy et al. | |
| 5,656,029 A | 8/1997 | Imran et al. | |
| 5,715,817 A | 2/1998 | Stevens-Wright et al. | |
| 5,735,795 A * | 4/1998 | Young et al. | 600/410 |
| 5,759,173 A * | 6/1998 | Preissman et al. | 604/103.07 |
| 5,826,576 A | 10/1998 | West | |
| 5,897,529 A | 4/1999 | Ponzi | |
| 5,906,590 A | 5/1999 | Hunjan et al. | |
| 5,938,616 A * | 8/1999 | Eaton et al. | 600/463 |
| 6,022,319 A | 2/2000 | Willard et al. | |
| 6,030,360 A | 2/2000 | Biggs | |
| 6,123,699 A * | 9/2000 | Webster, Jr. | 604/528 |
| 6,126,654 A | 10/2000 | Giba et al. | |
| 6,183,435 B1 | 2/2001 | Bumbalough et al. | |
| 6,251,092 B1 | 6/2001 | Qin et al. | |
| 6,261,255 B1 * | 7/2001 | Mullis et al. | 604/8 |
| 6,267,746 B1 | 7/2001 | Bumbalough | |
| 6,458,088 B1 | 10/2002 | Hurtak et al. | |
| 6,485,455 B1 | 11/2002 | Thompson et al. | |
| 6,551,271 B2 | 4/2003 | Nguyen | |
| 6,579,278 B1 | 6/2003 | Bencini | |
| 6,582,536 B2 | 6/2003 | Shimada | |
| 6,858,024 B1 | 2/2005 | Berg et al. | |
| 6,945,956 B2 | 9/2005 | Waldhauser et al. | |
| 6,976,987 B2 | 12/2005 | Flores | |
| 7,048,711 B2 | 5/2006 | Rosenman et al. | |
| 7,056,314 B1 * | 6/2006 | Florio et al. | 604/528 |
| 7,344,515 B2 | 3/2008 | Coyle | |
| 7,377,906 B2 | 5/2008 | Selkee | |
| 7,402,151 B2 | 7/2008 | Rosenman et al. | |
| 7,465,288 B2 | 12/2008 | Dudney et al. | |
| 7,591,784 B2 | 9/2009 | Butler | |
| 7,596,402 B2 | 9/2009 | Duerk et al. | |
| 7,615,044 B2 | 11/2009 | Scheibe et al. | |
| 7,682,319 B2 | 3/2010 | Martin et al. | |
| 7,682,358 B2 | 3/2010 | Gullickson et al. | |
| 7,691,095 B2 | 4/2010 | Bednarek et al. | |
| 7,803,130 B2 | 9/2010 | Ryan et al. | |
| 7,850,811 B2 | 12/2010 | Hart et al. | |
| 7,912,531 B1 * | 3/2011 | Chiu et al. | 600/423 |
| 7,955,305 B2 | 6/2011 | Moberg et al. | |
| 7,972,323 B1 | 7/2011 | Bencini et al. | |
| 8,016,784 B1 | 9/2011 | Hayzelden et al. | |
| 8,043,288 B2 | 10/2011 | Dando et al. | |
| 8,075,476 B2 | 12/2011 | Vargas | |
| 8,096,985 B2 | 1/2012 | Legaspi et al. | |
| 8,137,308 B2 | 3/2012 | Schultz | |
| 8,226,641 B2 | 7/2012 | Potter | |
| 8,260,399 B2 | 9/2012 | Karmarkar et al. | |
| 8,308,659 B2 | 11/2012 | Scheibe et al. | |
| 8,376,990 B2 | 2/2013 | Ponzi et al. | |
| 8,473,029 B2 * | 6/2013 | Gerhart et al. | 600/411 |
| 2005/0070844 A1 | 3/2005 | Chow et al. | |
| 2006/0264894 A1 | 11/2006 | Moberg et al. | |
| 2007/0073098 A1 | 3/2007 | Lenker et al. | |
| 2008/0161843 A1 | 7/2008 | Clague | |
| 2009/0163915 A1 | 6/2009 | Potter | |
| 2009/0171272 A1 | 7/2009 | Tegg et al. | |
| 2009/0287187 A1 | 11/2009 | Legaspi et al. | |
| 2009/0312698 A1 | 12/2009 | Farrell et al. | |
| 2010/0076408 A1 | 3/2010 | Krever et al. | |
| 2010/0168827 A1 | 7/2010 | Schultz | |
| 2010/0217261 A1 | 8/2010 | Watson | |
| 2011/0087270 A1 | 4/2011 | Penner et al. | |
| 2011/0264074 A1 * | 10/2011 | Tegg et al. | 604/523 |
| 2011/0264133 A1 | 10/2011 | Hanlon et al. | |
| 2011/0282176 A1 | 11/2011 | Tegg | |
| 2012/0010490 A1 | 1/2012 | Kauphusman et al. | |
| 2012/0017923 A1 | 1/2012 | Sobe | |
| 2012/0089125 A1 | 4/2012 | Scheibe et al. | |
| 2012/0123327 A1 | 5/2012 | Miller | |
| 2012/0130218 A1 | 5/2012 | Kauphusman et al. | |
| 2012/0172717 A1 | 7/2012 | Gonda | |
| 2012/0190927 A1 | 7/2012 | Uihlein | |
| 2012/0226228 A1 | 9/2012 | Butler | |
| 2012/0310212 A1 | 12/2012 | Fischell et al. | |
| 2013/0018306 A1 | 1/2013 | Ludwin | |
| 2013/0116705 A1 | 5/2013 | Salahieh et al. | |
| 2013/0165857 A1 | 6/2013 | O'Donnell et al. | |
| 2013/0165922 A1 | 6/2013 | Falwell et al. | |

FOREIGN PATENT DOCUMENTS

| | | |
|---|---|---|
| EP | 0713408 A1 | 5/1996 |
| EP | 1676596 A1 | 5/2006 |
| EP | 1803481 A2 | 4/2007 |
| WO | WO 2007-046953 A2 | 4/2007 |
| WO | WO 2010-082150 | 7/2010 |
| WO | WO 2011-051872 | 5/2011 |
| WO | WO 2011-055143 | 5/2011 |
| WO | WO 2012-158263 A1 | 11/2012 |

OTHER PUBLICATIONS

International Search Report and Written Opinion issued by the International Search Authority, U.S. Receiving Office, regarding corresponding patent application Serial No. PCT/US2012/069487, dated Feb. 26, 2013, 13 pages.

* cited by examiner

MRI COMPATIBLE HANDLE AND STEERABLE SHEATH

CROSS REFERENCE TO RELATED APPLICATIONS

This application is a continuation-in-part of U.S. application Ser. No. 13/819,981, filed on Feb. 28, 2013, which claims the benefit of PCT application Serial No.: PCT/US2012/069487, filed on Dec. 13, 2012, which claims the benefit of U.S. Provisional application Ser. No. 61/576,161, filed on Dec. 15, 2011. This application is also a continuation of PCT application Serial No.: PCT/US2013/074331, filed on Dec. 11, 2013. The entireties of all of the foregoing are hereby incorporated by reference.

FIELD OF THE INVENTION

This invention relates to deflectable medical catheters, namely steerable sheaths used in interventional vascular procedures to deliver tools (e.g. electrophysiology catheters, guidewires, balloons catheters, stents, instruments, etc.) into the human body and handles for operating the steerable sheath. More particularly, the present invention is related to a family of sheaths that is safe for use in the magnetic resonance environment and handles for operating the sheaths, as the materials used in the invention are compatible with strong electromagnetic fields.

BACKGROUND OF THE INVENTION

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

A variety of MRI techniques are being developed as alternatives to X-ray imaging for guiding interventional procedures. For example, as a medical device is advanced through the patient's body during an interventional procedure, its progress may be tracked so that the device can be delivered properly to a target site. Once delivered to the target site, the device and patient tissue may be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that may result from an interaction between the RF field of the MRI scanner and the medical device (RF-induced heating), especially medical devices that have elongated conductive structures, such as braiding and pull-wires in catheters and sheaths.

The RF-induced heating safety risk associated with elongated metallic structures in the MRI environment results from a coupling between the RF field and the metallic structure. In this case several heating related conditions exist. One condition exists because the metallic structure electrically contacts tissue. RF currents induced in the metallic structure may be delivered into the tissue, resulting in a high current density in the tissue and associated Joule or Ohmic tissue heating. Also, RF induced currents in the metallic structure may result in increased local specific absorption of RF energy in nearby tissue, thus increasing the tissue's temperature. The foregoing phenomenon is referred to as dielectric heating. Dielectric heating may occur even if the metallic structure does not electrically contact tissue, such metallic braiding used in a deflectable sheath. In addition, RF induced currents in the metallic structure may cause Ohmic heating in the structure, itself, and the resultant heat may transfer to the patient. In such cases, it is important to attempt to both reduce the RF induced current present in the metallic structure and/or eliminate it all together by eliminating the use of metal braid and long metallic pull-wires.

The static field of the MRI will cause magnetically induced displacement torque on any device containing ferromagnetic materials and has the potential to cause unwanted device movement. It is important to construct the sheath and control handle from non-magnetic materials, to eliminate the risk of unwanted device movement.

When performing interventional procedures under MRI guidance, clinical grade image quality must be maintained. Conventional steerable sheaths are not designed for the MRI and may cause image artifacts and/or distortion that significantly reduce image quality. Constructing the sheath from non-magnetic materials and eliminating all potentially resonant conductive structures allows the sheath to be used during active MR imaging without impacting image quality. Similarly, it is as important to ensure that the control handle is also constructed from non-magnetic materials thereby eliminating potentially resonant conductive structures that may prevent the control handle being used during active MR imaging.

Conventional steerable sheaths utilize metallic braiding for torque delivery and kink resistance; metallic pull-wires and anchor bands for distal tip deflection; metallic marker bands for fluoroscopy visualization; and ferromagnetic metals in the control handle to minimize cost. Thus because the pull-wires incorporate a conductive materials they will react with the RF field of the MRI scanner and result in RF heating and the associated danger to patients and image degradation and artifacts. Additionally, the control handles incorporate ferromagnetic materials that may be attracted to the strong static magnetic field of the MRI scanner. Moreover, the fluoroscopy marker bands in conventional designs may not be compatible with the MR environment due to static field interactions and image degradation and, therefore, are not optimal for visibility in the MRI environment. Therefore, visualization within the MR environment may require the use of either passive or active MR tracking techniques. Passive tracking techniques include passive markers that may lead to image distortion due to direct currents or the use of inductively coupled coils. Active tracking is more robust than passive tracking but involve resonant RF coils that are attached to the device and directly connected to an MR receiver allowing for the determination of the three-dimensional coordinates of the resonant RF coils within the scanner. To the inventors' knowledge neither active nor passive tracking techniques are presently utilized in conventional steerable sheaths or control handles.

Thus, there is a need for a steerable sheath catheter and control handle that are built with MR compatible materials to eliminate the magnetic resonance environment limitations of conventional sheaths while maintaining other characteristics of conventional sheaths. In particular, there is a need for a more efficient way to delivery tools and other instruments into a body cavity or passageway during treatment in an MR environment.

BRIEF SUMMARY OF THE INVENTION

The foregoing need is addressed by the steerable sheath and control handle in accordance with the invention. In one aspect of the invention a steerable sheath is provided that may be used in an MRI environment to deliver a variety of tools (catheters, guidewires, implantable devices, etc.) into the lumens of the body. In a further aspect of the invention, the steerable sheath comprises a reinforced polymer tube in which the reinforcing material is non-metallic based (Kevlar, PEEK, Nylon, fabric, polyimide, etc.) or a hybrid of metallic and non-metallic materials and the reinforcing geometry may comprise a braid, a coil, or a slit tube that mimics a coil and combinations of the foregoing. In yet another aspect of the invention, the reinforced polymer tube may also be segmented with varying flexibility along its length to provide the user with the ability to deflect the catheter in a region in which the segment is more flexible than other segments. In yet another aspect of the invention the polymer tube may also include one or more passive visualization markers along the length of the tube and/or one or more active visualization markers along the length of the tube.

The steerable sheath in accordance with the invention also includes one or more pull-wires which are coupled with the reinforced tube and that allow the user to manipulate and deflect the polymer tube. In one aspect of the invention, the pull-wires are preferably made of a non-metallic material (Kevlar, PEEK, Nylon, fabric, etc.). One or more internal pull-wire lumens are positioned within the polymer tube construct and allow the user to manipulate the pull-wires to move smoothly during actuation. One or more anchor points connect the pull-wire in the distal portion of the polymer tube.

In another aspect of the invention a control handle on the proximal end of the reinforced tube operates longitudinal movement of the pull-wire(s). In one aspect of the invention, the handle includes paramagnetic or diamagnetic materials or combinations of paramagnetic and diamagnetic materials.

In another aspect of the invention, an MR compatible deflectable catheter is provided. The MR compatible deflectable catheter includes a steerable sheath having a tubular shaft, said tubular shaft receiving first and second longitudinal movement wires operably coupled to a distal end thereof; a control handle having a main body configured to receive first and second rack screws, said second rack screw including a threaded portion on an outer surface at a distal end thereof; said first longitudinal movement wire operably coupled to said first rack screw and said second longitudinal movement operably coupled to said second rack screw; and a rotatable adjustment knob operably engageable with said control handle, said rotatable adjustment knob having an internal threaded portion matingly engageable with the threaded portion of said second rack screw, said rotatable adjustment knob moveable between a first position in which the internal thread is configured to engage the thread on the outer surface of said second rack screw and cause said second rack screw to move proximally to cause proximal longitudinal movement of the second longitudinal movement wire and a second position in which the internal thread is configured to move said second rack screw in a distal direction to release tension on the second longitudinal movement wire In another aspect of the invention a method of using the MR compatible steerable sheath is also provided. A method of deflecting a deflectable catheter includes providing a steerable sheath having a tubular shaft, the tubular shaft receiving first and second longitudinal movement wires having first and second ends, the first end operably coupled to a distal end of the tubular shaft; providing a control handle having a main body configured to receive first and second rack screws, the first and second rack screws including an inner threaded channel and an outer surface, the outer surface of the second rack screw including a thread at a distal end thereof, wherein the second end of the first longitudinal movement wire is operably coupled to the first rack screw and wherein the second end of the second longitudinal movement is operably coupled to the second rack screw; first and second pinion gears coupled to the tubular shaft of the steerable sheath and operably engageable with the inner threaded channel of the first and second rack screws; and a rotatable adjustment knob having an internal thread engageable with the threaded outer surface of the second rack screw and moveable between a first position and second position; rotating the rotatable adjustment knob in the first position to cause engagement of the outer thread of the second rack screw such that the second rack screw moves proximally longitudinally, wherein the proximal longitudinal movement of the second rack screw causes engagement of the pinion gears on the inner threaded channel; causing the pinion gears to movably advance along the threaded internal channel in the distal direction relative to the second rack screw and in the proximal direction relative the first rack screw thereby causing the first rack screw to move distally thereby releasing tension on the first longitudinal movement wire and causing the second rack screw to move proximally thereby causing tension on the second longitudinal movement wire to moveably cause the distal end of the steerable sheath to deflect to at least 180 degrees in a first direction from a longitudinal axis of the tubular shaft; rotating the rotatable adjustment knob in the second direction; causing the pinion gears to movably advance along the threaded internal channel in the proximal direction relative to the second rack screw and in the distal direction relative to the first rack screw thereby causing the second rack screw to move distally thereby releasing tension on the second longitudinal movement wire and causing the first rack screw to move proximally thereby causing tension of the first longitudinal movement wire thereby causing the distal end of the steerable sheath to deflect to at least 180 degrees in a second direction from a longitudinal axis of the tubular shaft.

These and other features of the invention will now be described in detail with reference to the accompanying Figures.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Numerous structural variations of an MR compatible steerable sheath and control handle in accordance with the invention are contemplated and within the intended scope of the invention. Those of skill in the art will appreciate that the exemplary control handle may be coupled to other types of steerable sheaths. In addition, those of skill in the art will appreciate that the exemplary steerable sheath may be couple with other control handles. Therefore, for purposes of discussion and not limitation, an exemplary embodiment of the MR compatible steerable sheath and control handle will be described in detail below.

Figure 1:
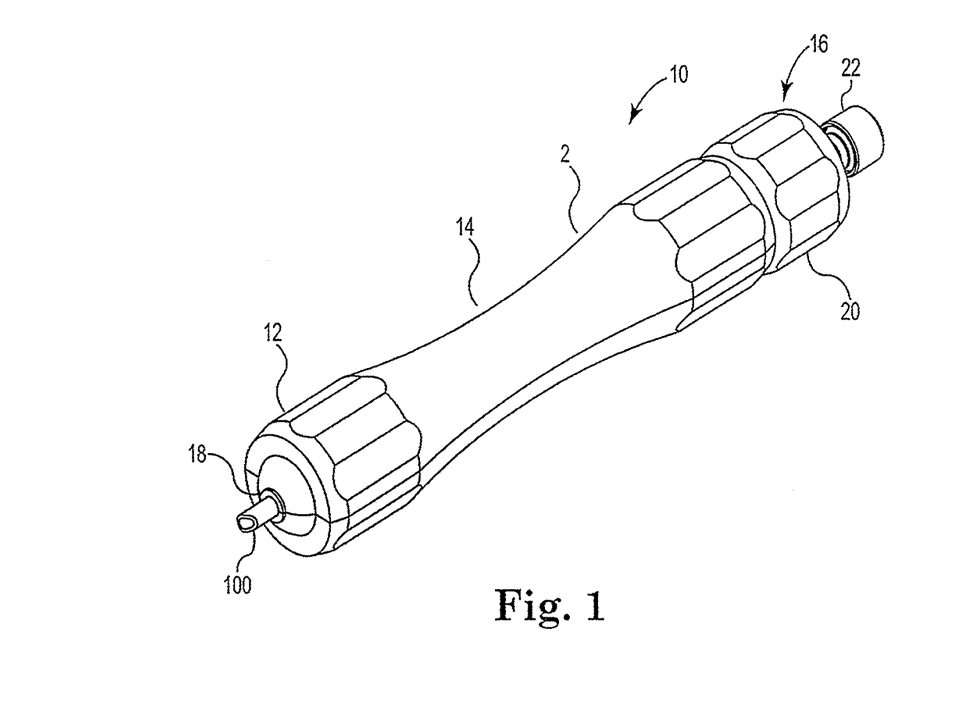
FIG. 1 is a perspective view of a control handle that may operably coupled with the steerable sheath according to an aspect of the invention.

Referring now to FIG. 1, the control handle 10 in accordance with the invention includes a cover 2 as illustrated in FIG. 1. Cover 2 includes distal portion 12, hand-graspable middle region 14, and proximal end 16. Distal portion 12 includes aperture 18 through which steerable sheath 100 exits. Proximal end 16 includes rotatable adjustment knob 20 and port 22. Rotatable adjustment knob 20 is operably coupled to a proximal end (not shown) of steerable sheath 100 such that rotation of the knob causes movement of steerable sheath 100 as hereinafter described. Port 22 includes an aperture therethrough for receiving a medical device such as by way of example an MR-compatible electrode circuit such as that disclosed in U.S. Publn. No. 2011/0046707, the entirety of which is hereby incorporated by reference.

Figure 2:
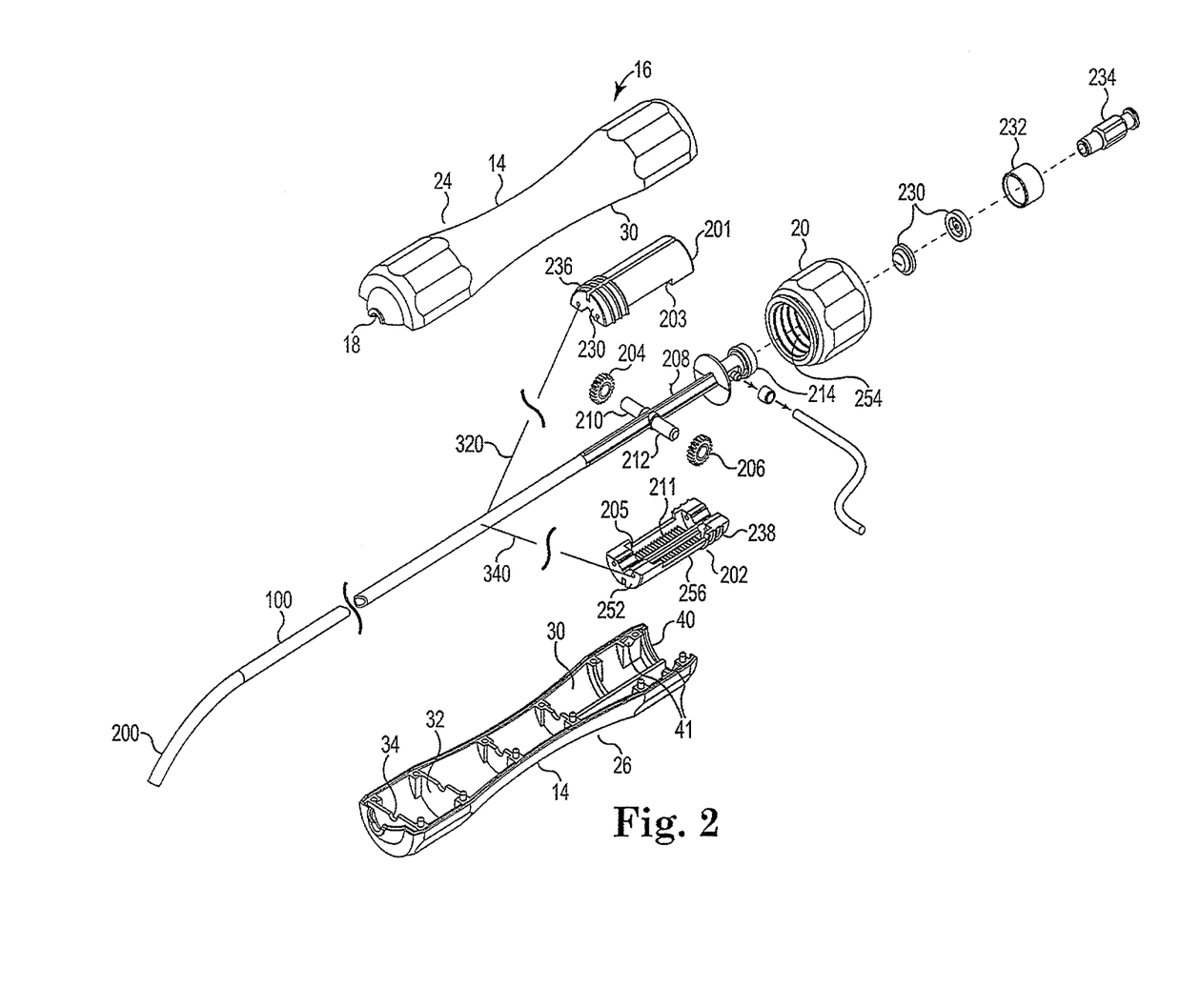
FIG. 2 is an exploded perspective view of the control handle and steerable sheath according to an aspect of the invention.

Referring now to FIG. 2 an exploded view of the control handle 10 and steerable sheath 100 in accordance with the invention is shown. Cover 2 of control handle 10 includes a first mating portion 24 and a second mating portion 26. Those of skill in the art will appreciate, however, that cover 2 may include any number of mating portions and still be within the scope of the invention. Each of the first and second mating portions 24, 26 include an inner face 30 having a plurality of inserts 32 fixedly coupled to inner face 30. As depicted, inserts 32 include a receiving groove therewithin. When first mating portion and second mating portion are operably coupled, receiving groove 34 forms a lumen into which steerable sheath 100 is received. First mating portion 24 and second mating portion 26 when mated form an internal recess 40 at a distal end thereof, which accommodates first and second rack screws 201, 202. It should be noted that the distal threads 236 of the first rack screw 201, although shown, have no function. First and second rack screws 201, 202 are mirror images of each other. Therefore, the distal threads 236 of the first rack screw 201 are present to reduce the cost of manufacturing so that first and second rack screws 201, 202 can be made from the same mold. Control handle 10 further includes first and second pinion gears 204, 206, t-valve axel 208, first and second pegs 210, 212, t-valve 214, tube retainer 216, tube 218, and rotatable adjustment knob 20. Rotatable adjustment knob 20 receives seals 230, seal cap 232 and fitting 234. First and second pegs 210, 212 are operably coupled to t-valve axel 208. Groove 41 receives pegs 210, 212. First and second pegs 210, 212 receive pinion gears 204 and 206. Tube 218 attaches to a stopcock in t-valve which connects to a syringe for flushing or aspirating the steerable catheter.

As may be seen in FIG. 2, second rack screw 202 includes distal threads 238 on an outer surface thereof. Threaded distal end 238 is operably received by an inset 40 in the proximal end of first and second mating covers 24, 26. An internal central channel of each of first and second rack screws 201, 202 includes a threaded portion 211 that threadably receives pinion gears 204, 206 in operation. First and second rack screws 201, 202 include notched portion 203, 205. First and second pull wires 320, 340 are routed and are operably coupled to ends 230, 252 of each rack screw 201, 202, respectively. Pinion gears 204, 206 are received by pegs 210, 212 operably coupled to t-valve axel 208. In operation, posts 210, 212 are received by and move longitudinally on notched portion 203, 205 respectively. This allows threaded pinion gears 204, 206 to be received by and move longitudinally along the threaded central channel of each of first and second rack screws 201, 202.

Rotatable adjustment knob 20 includes internal threads 254 circumferentially disposed about an inner wall thereof. Internal threads 254 will engage the distal threads 238 of the second rack screw 202. As the rotatable adjustment knob is rotated clock-wise the internal adjustment knob threads 254 engage the distal threads 238 of the second rack screw 202 causing longitudinal, proximal movement of rack screw 202. As the rotatable adjustment know is rotated counter-clockwise the internal threads (still engaged with the distal threads 238 of the second rack screw 202) causes longitudinal, distal movement of rack screw 202.

Figure 3:
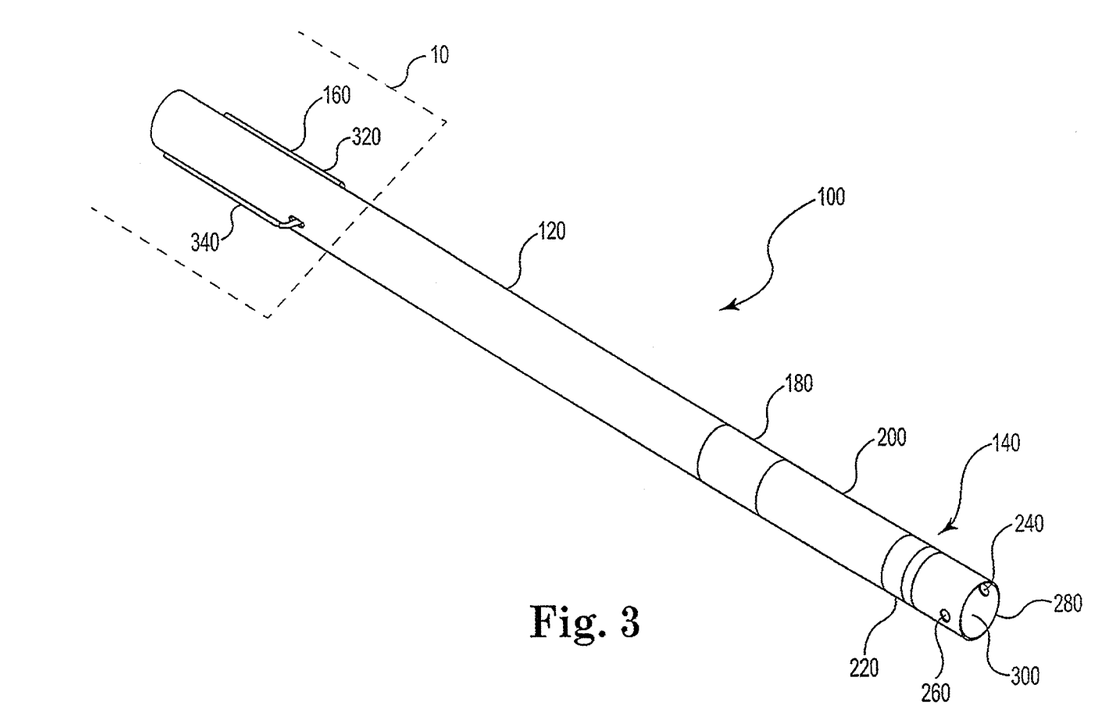
FIG. 3 is a perspective view of the steerable sheath according to an aspect of the invention.

Referring now to FIG. 3, the steerable sheath 100 in accordance with the invention will now be explained. Steerable sheath 100 may be used in an MRI environment to deliver a variety of tools such as catheters, guide wires, implantable devices, etc. into cavities and passageways of a patient body. The steerable sheath 100 includes a deflectable tip portion 200 that is able to bend at least 180 degrees offset from the longitudinal axis of the catheter sheath 100. This flexibility allows the medical professional to make very tight turns to deliver the aforementioned tools to the cavities and passageways of the patient body.

Referring again to FIG. 3 a perspective view of an MR compatible steerable sheath that is suitable for use in an MRI environment is depicted. The MR compatible steerable sheath 100 in accordance with the invention broadly includes tubular shaft 120 with distal 140 and proximal ends 160. Tubular shaft 120 includes an outer diameter 130, an inner diameter 150 and defines a central lumen 300 therewithin. Tubular shaft may be constructed of a variety of polymers such as pebax, polyurethane, nylon, derivatives thereof and combinations of the foregoing.

Distal end 14 includes transition section 180, deflectable tip portion 200, and magnetic marker 220. Pressure relief holes 240, 260 may be formed in the tubular shaft 120 at the distal end 140. Those of skill in the art will appreciate that while only two pressure relief holes 240, 260 are shown there may any number of pressure relief holes formed and still be within the scope of the invention. When retracting an item housed by the sheath 100, such as a catheter or MR active tracking system, pressure may form at the end of the sheath thereby drawing or sucking in tissue. Pressure relief holes 240, 260 are designed to reduce this pressure thereby ameliorating the risk of tissue damage.

Transition section 180 is optionally included for purposes of manufacturability. The deflectable tip section 20 has a significantly lower durometer making it more malleable and flexible than the main body portion 170 of tubular shaft 120 which has a higher durometer or, in other words, quite stiff. As a consequence, these two sections do not bond to one another well. Transitional section 180 has a mid-range durometer allowing it to bond well to both the deflectable tip section 200 and the main body 170 of the tubular shaft 120. Those of skill in the art will appreciate that the transition section 180 may be of any length desired so as to provide an adequate transition between the distal tip portion 200 and the main body portion 170. In one exemplary embodiment transition section may range from about 0.25 to about 0.75 inches. In addition, those of skill in the art will appreciate that transition section may be eliminated and the deflectable tip section 200 may be coupled to the main body 170 of tubular shaft 120 by means known to those of skill in the art without departing from the spirit of the invention.

Steerable sheath 100 includes central lumen 300 therewithin. In one aspect of the invention, the inner diameter 150 of the tubular shaft 120 is approximately 6 French or greater but those of skill in the art will appreciate that varying internal diameters may be used depending on the particular application without departing from the scope of the present invention. Central lumen 300 may include one or more liners (not shown) disposed therewithin to allow for easier movement of instruments therethrough. Liners may comprise materials made from polytetrafluoroethylene (PTFE), fluorinated ethylene propylene copolymer (FEP), nylons and combinations of the foregoing. Alternatively, the lumen 300 may be coated with any such polymers. The polymer tubular shaft 120 may also include one or more passive visualization markers, such as a ferrous or magnetic marker 220, disposed circumferentially about the tubular shaft 120 at one or more locations along the length thereof and/or one or more active visualization markers such as an active tracking coil along the length of the tube. An active tracking coil may comprise one or more small antennas integrated into the device and include traces on a circuit board, coiled wire, and/or a dipole. If an active visualization marker is used, one or more devices may be included in the conductors to mitigate RF field heating may be included. Such devices include chokes, transformers, impedances, and other such devices known to those of skill in the art. One or more fluoroscopy markers (not shown) may also be included along the length of the polymer tubular shaft 12.

One or more optional fluid ports (not shown) may be located on the proximal end 16 of the tubular shaft 12 to allow for homeostasis of the sheath with the patient body. The fluid port(s) allows access for the user or physician to aspirate blood from the steerable sheath lumen 30 and flush with saline. Aspirating and flushing of the sheath prevents air from entering the body before and during insertion of a tool and/or catheter.

Figure 4:
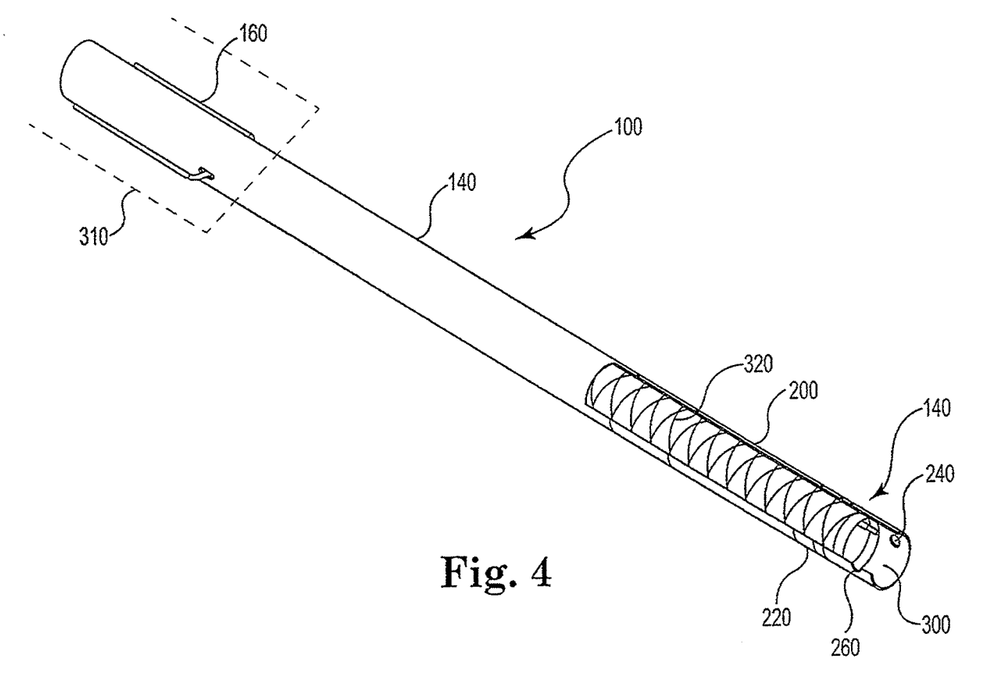
FIG. 4 is a perspective view of the steerable sheath according to an aspect of the invention with the steerable distal tip cut away to show detail.

Referring now to FIG. 4 a cut away view of the steerable sheath 100 in accordance with the invention depicts a reinforcement construct 320 of the tubular shaft 120. As shown, the geometry of the reinforcement construct 320 is braided but those of skill in the art will appreciate that the reinforcement construct 320 may comprise other configurations so long as it imparts the necessary deflectability to the tubular shaft 120 at the distal end. For example the reinforcement geometry may be a coil or a slit tube that mimics a coil or combinations of the foregoing. The reinforcement of the tubular shaft 120 may extend from the distal end 140 to the proximal end 160 or may extend from the deflectable tip section 200 to approximately the transition section 180 of the tubular shaft 12.

The material used in the reinforcement construct 320 may be non-metallic such as Kevlar, PEEK, Nylon, fabric, polyimide, fiber optic, silica glass and the like or may also be hybrid of metallic, such as stainless steel, and non-metallic materials. Those of skill in the art will appreciate that, the reinforced polymer tubular shaft 140 may be segmented and each segment may be constructed with varying flexibility along the segment to provide the user with the ability to deflect the sheath in a region in which the segment is more flexible than in other segments. Varying flexibility and thus deflectability may be accomplished by having braids or coils that have greater braiding or coils per sq. cm than in other segments where the braiding or coiling would be less per sq. cm. Flexibility and deflectability may also be accomplished by the varying durometers as herein described.

Figure 5A:
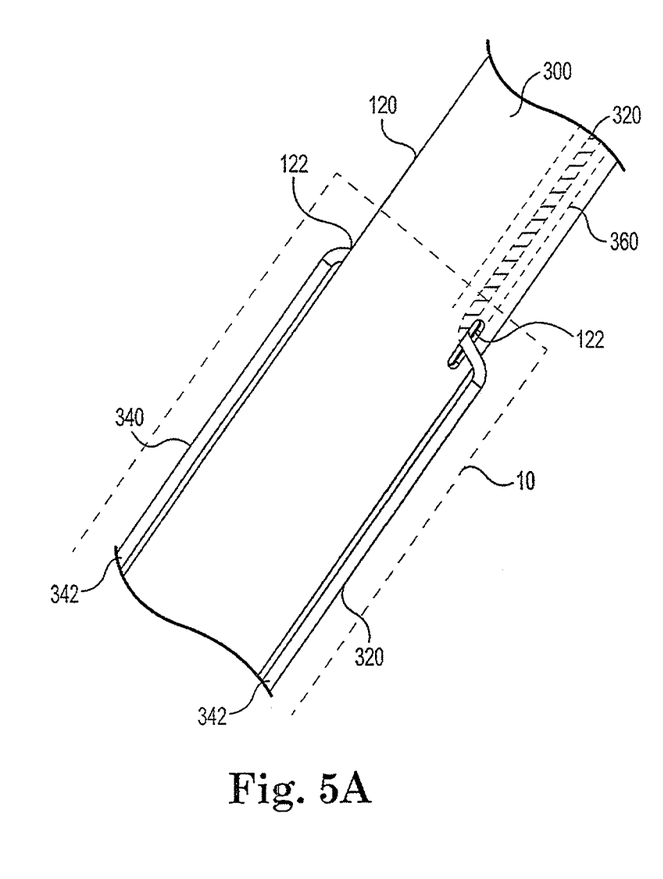
FIG. 5A is an enlarged view of the pull wires at the proximal end of the steerable sheath in accordance with the invention.
Figure 5B:
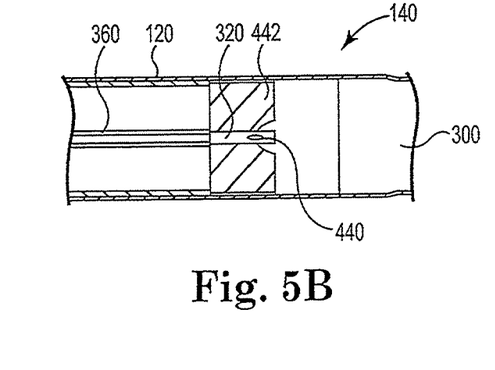
FIG. 5B is a detailed view of a pull ring that provides a contact point between the pull wire and the distal end of the steerable sheath in one aspect of the invention.

Referring now to FIG. 5A, an enlarged view of the proximal end 160 of the steerable sheath 100 in accordance with the invention is depicted. Proximal end 160 of the steerable sheath is operably coupled to control handle 10 depicted in dashed lines and as hereinafter described. The steerable sheath 100 in accordance with the invention includes one or more pull-wires 320, 340 which are operably coupled at a pull-wire proximal end 342 to the control handle 10 as hereinafter will be described. The portion of the pull-wires 320, 340 that are operably coupled to the control handle exit the tubular body 120 at opening 122. The portion of the pull-wires 320, 340 that are operably coupled to pull ring 440 (as best seen in FIG. 5B) extend through a lumen constructed from a sheet of polymeric material fastened to an inner portion of tubular shaft 120 for a length thereof and enter tubular shaft 120 through entrance holes 330, 350 on opposing sides of tubular shaft 120. Pull-wires 320, 340 allow the user to manipulate and deflect the one or more flexible segments along the length of the polymer tubular shaft 120 and in particular the deflectable tip portion 200. In one aspect of the invention, the pull-wires 320, 340 are preferably made of a non-metallic material (Kevlar, PEEK, Nylon, fabric, etc.).

One or more internal pull-wire lumens 360 are constructed of a flexible, non-metallic material such as PTFE. Internal pull-wire lumens 360 facilitate smooth manipulation of the pull-wires 320, 340 during actuation. Internal pull-wire lumens 360 have an outer diameter of approximately 0.12 inches and an inner diameter of approximately 0.010 inches. However, those of skill in the art will appreciate that the dimensions of the internal pull-wire lumens 360 may vary with the dimensions of both the pull-wires 320, 340 and the tubular shaft 120 so long as they are dimensioned to house the pull-wires and allow pull-wires to move smoothly during actuation.

Referring to FIG. 5B, a side view of the distal end of the steerable sheath in accordance with the invention is shown. Pull wires 320, 340 are operably coupled at their distal end to an opening 440 in pull ring 442 positioned within lumen 300 at the deflectable tip 200 end of the steerable sheath 100.

Referring now to FIGS. 6-9 an exemplary control handle 31 for operating the steerable sheath is disclosed. As discussed in reference to FIG. 2, control handle 310 allows the user to control the longitudinal movement of pull-wires 320, 340 which in turn "pull" or deflect the distal end 140 of the steerable sheath 100 in opposite directions. Control handle 310 is positioned on the proximal end of the steerable sheath 100 and operates longitudinal movement of the pull-wire(s) and correspondingly, directional movement of the steerable sheath 100. In one aspect of the invention, control handle 310 includes paramagnetic or diamagnetic materials or combinations of paramagnetic and diamagnetic materials.

Figure 6:
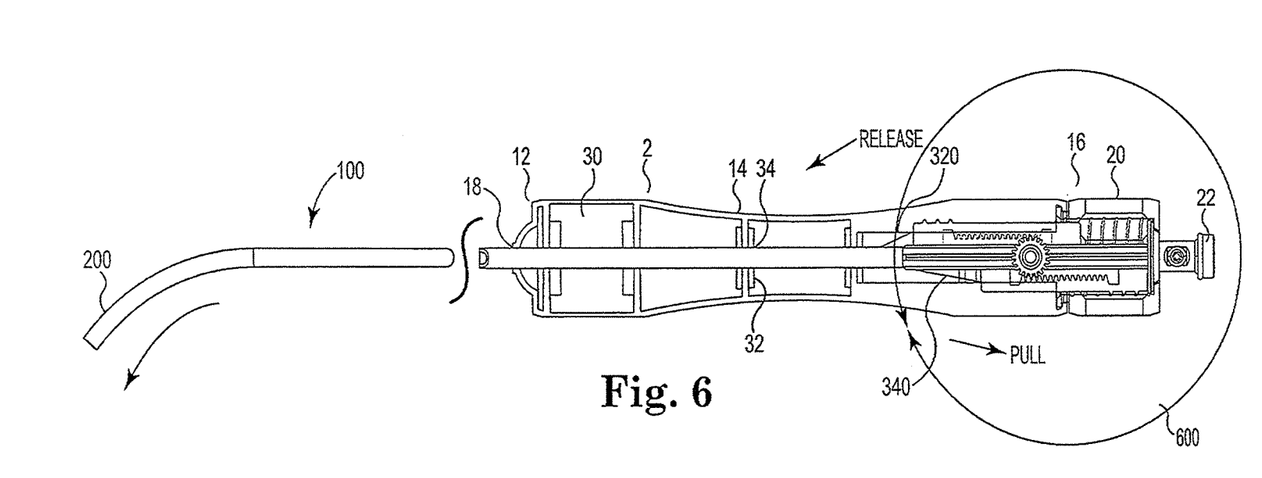
FIG. 6 is a side view of the control handle and steerable sheath according to an aspect of the invention.
Figure 7:
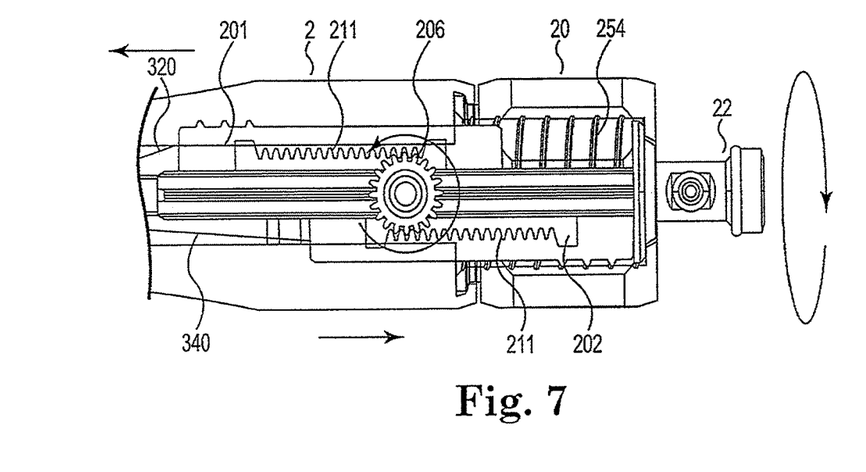
FIG. 7 is an enlarged view of the control handle mechanical structure denoted by 600 in FIG. 6 and showing clockwise rotation of rotatable knob.

Referring now to FIGS. 6 and 7, FIG. 7 is an enlarged view of the control handle of FIG. 6 denoted at numeral 600. Adjustment knob 20 is rotated in the clockwise direction, which causes internal threads 254 to engage threads 238 of second rack screw 202 and longitudinal, proximal movement of the second rack screw. At the same time, the pinion gear is engaged by the longitudinal movement of the second rack screw. This causes the first rack screw to move in the opposite direction, i.e. distally. Distal movement of the first rack screw releases tension in the first pull wire 320. As the rotatable adjustment knob 20 continues to be rotated in a clockwise direction pinion gears 204, 206 operably engage threaded portion 211 of first and second rack screws and fixes the rate of linear travel of opposite pinion gear as best seen in FIG. 7.

As rotatable adjustment knob 20 is rotated in the clockwise direction and engages rack screws which in turn engage pinion gears, second pull wire 340 is pulled toward the proximal direction as best seen in FIG. 6. In turn, the tension on first pull wire 320 is released. As second pull wire 340 is pulled in the proximal direction deflectable tip moves in one direction, shown as a downward direction in FIG. 6 however those of skill in the art will appreciate that the direction of deflectable tip is relative to how or the direction in which the user is holding the handle 10. When pinion gears 204, 206 abut stop 205 in second rack screw 202 further movement of rotatable adjustment knob 20, pinion gears 204, 206 and deflectable tip is halted.

Figure 8:
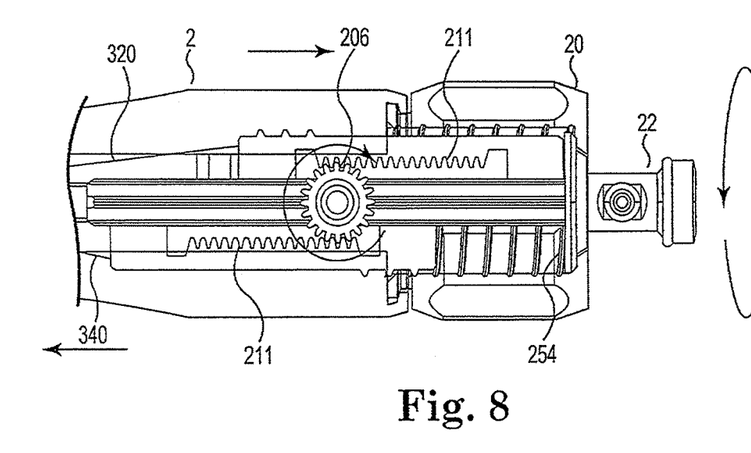
FIG. 8 is an enlarged view of the control handle mechanical structure denoted by 800 in FIG. 6 and showing counterclockwise rotation of rotatable knob.
Figure 9:
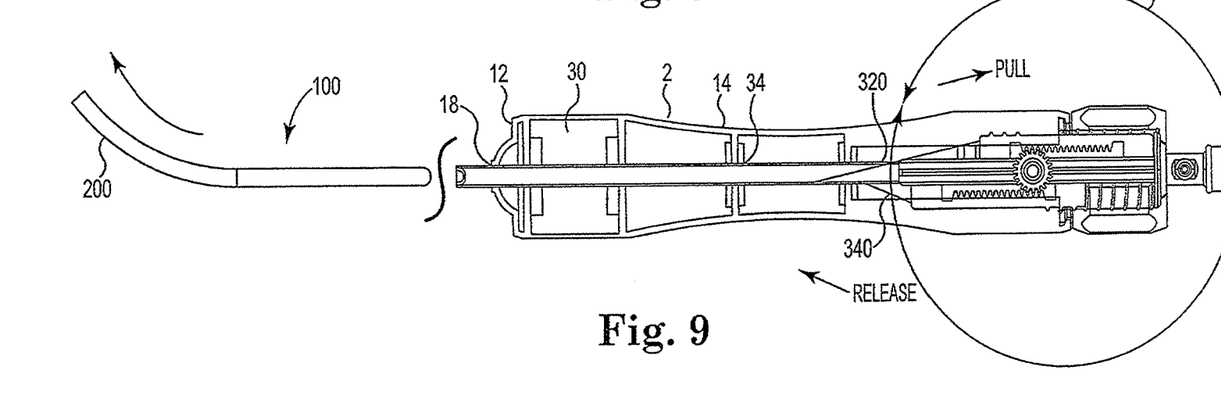
FIG. 9 is a side view of the control handle according to an aspect of the invention showing the function of the pull wire.

Referring now to FIGS. 8 and 9 the opposite function is illustrated. Adjustment knob 20 is rotated in the counter-clockwise direction, internal threads 254 engage threads 238 of second rack screw 201 causing longitudinal, distal movement. As the rotatable adjustment knob 20 continues to be rotated in a counter-clockwise direction, pinon gears 204, 206 once again operably engage threaded portion 211 of first and second rack screws which fixes the rate of linear travel of the opposite pinion gear as best seen in FIG. 8.

As rotatable adjustment knob 20 is rotated in the counter-clockwise direction first pull wire 320 is pulled toward the proximal direction as best seen in FIG. 9. In turn, the tension on second pull wire 340 is released. As first pull wire 320 is pulled in the proximal direction deflectable tip moves in the opposite direction, shown as an upward direction in FIG. 9. However those of skill in the art will appreciate that the direction of deflectable tip is relative to how, or the direction in which, the user is holding the handle 10. When pinion gears 204, 206 abut stop 203 in first rack screw 202 further movement of rotatable adjustment knob 20, pinion gears 204, 206 and deflectable tip is halted.

Although the present invention has been described with reference to preferred embodiments, workers skilled in the art will recognize that changes may be made in form and detail without departing from the spirit and scope of the invention.

We claim:

1. A MR compatible deflectable catheter comprising:
   a steerable sheath having a tubular shaft defining a longitudinal axis, said tubular shaft receiving first and second longitudinal movement wires operably coupled to a distal end thereof;
   a control handle having a main body configured to receive first and second rack screws, said first and second rack screws being mechanically coupled to each other such that movement of said second rack screw along the longitudinal axis of the tubular shaft causes movement of said first rack screw in an opposite direction along the longitudinal axis of the tubular shaft, said second rack screw including a threaded portion on an outer surface at an end thereof;
   said first longitudinal movement wire operably coupled to said first rack screw and said second longitudinal movement wire operably coupled to said second rack screw; and
   a rotatable adjustment knob operably engageable with said control handle, said rotatable adjustment knob having an internal threaded portion matingly engageable solely with the threaded portion of said second rack screw, said rotatable adjustment knob solely rotatably moveable between a first position and a second position in which the internal thread is configured to engage solely the thread on the outer surface of said second rack screw,
   wherein said first position causes said second rack screw to move proximally along the longitudinal axis of the tubular shaft which in turn causes said first rack screw to move distally along the longitudinal axis of the tubular shaft and proximal movement of said second rack screw is configured to tension and cause proximal longitudinal movement of the second longitudinal movement wire,
   and further wherein said second position is configured to move said second rack screw distally along the longitudinal axis of the tubular shaft which in turn causes said first rack screw to move proximally and distal movement of said second rack screw is configured to release tension on the second longitudinal movement wire.

2. The MR compatible deflectable catheter of claim 1 wherein said proximal longitudinal movement of said second longitudinal movement wire is configured to causes the distal end of said steerable sheath to deflect about 180 degrees from a longitudinal axis of the tubular shaft in a first direction.

3. The MR compatible deflectable catheter of claim 1 wherein said tubular shaft further includes a pull ring at a distal end thereof and said first and second longitudinal movement wires are operably coupled thereto.

4. The MR compatible deflectable catheter of claim 1 wherein said tubular shaft further includes two internal lumens positioned on opposite sides of said tubular shaft for housing said first and second longitudinal movement wires.

5. The MR compatible deflectable catheter of claim 2 wherein said tubular shaft includes a reinforcement construct at the distal end thereof configured to allow said steerable sheath to deflect at least 180 degrees from the longitudinal axis of the tubular shaft.

6. The MR compatible deflectable catheter of claim 5 wherein said reinforcement construct is selected from a braided configuration, a coiled configuration, a slit tube configuration and combinations of the foregoing.

7. The MR compatible deflectable catheter of claim 1 wherein said shaft includes one or more pressure relief holes.

8. The MR compatible deflectable catheter of claim 1 wherein said shaft includes a transition section having a durometer that is higher than the durometer of the distal end of the shaft and less than the durometers of the proximal end of said shaft.

9. The MR compatible deflectable catheter of claim 1 wherein a lumen of said tubular shaft is lined or coated with a hydrophilic material.

10. The MR compatible deflectable catheter of claim 1 wherein said tubular shaft further includes a ferrous marker, a magnetic marker or a fluoroscopy marker disposed on said tubular shaft.

11. The MR compatible deflectable catheter of claim 1 wherein said tubular shaft further includes an active tracking coil along a length, said active tracking coil comprising chokes, transformers, impedances and combinations of the foregoing.

12. The MR compatible deflectable catheter of claim 11 wherein said active tracking coil comprises traces on a circuit board, a coiled wire, a dipole and combinations of the foregoing.

13. The MR compatible deflectable catheter of claim 1 wherein said tubular shaft further includes one or more fluid ports configured to allow for hemostasis of the steerable sheath.

14. The MR compatible deflectable catheter of claim 5 wherein said reinforcement construct comprises a non-metallic material selected from Kevlar, PEEK, Nylon, fabric, polyimide, fiber optic, silica glass and combinations of the foregoing.

15. The MR compatible deflectable catheter of claim 5 wherein said reinforcement construct comprises a combination of metallic and non-metallic materials.

16. The MR compatible deflectable catheter of claim 1 further comprising first and second pinion gears operably engageable with an inner threaded channel of said first and second rack screws, wherein the proximal longitudinal movement of said second rack screw is configured to cause engagement of said first and second pinion gears to cause said first rack screw to move distally and release tension on said first longitudinal movement wire.

17. The MR compatible deflectable catheter of claim 16 wherein said second position of said adjustable rotation knob is configured to cause longitudinal distal movement of said second rack screw and release of tension on said second longitudinal movement wire.

18. The MR compatible deflectable catheter of claim 17 wherein proximal movement of said second rack screw is configured to release tension on said first longitudinal movement wire.

19. The MR compatible deflectable catheter of claim 1 wherein said distal movement of said second rack screw is configured to cause the distal end of said steerable sheath to deflect at least 180 degrees from a longitudinal axis of the tubular shaft in a second direction.

* * * * *